United States Patent
Standar

(10) Patent No.: US 7,891,874 B2
(45) Date of Patent: Feb. 22, 2011

(54) MAMMOGRAPHY APPARATUS COMPRESSION TRAY, AND MOUNTING AND MANUFACTURING METHOD THEREFOR

(75) Inventor: Robert Standar, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 63 days.

(21) Appl. No.: 12/269,942

(22) Filed: Nov. 13, 2008

(65) Prior Publication Data

US 2009/0136005 A1    May 28, 2009

(30) Foreign Application Priority Data

Nov. 23, 2007   (DE) .................. 10 2007 056 433

(51) Int. Cl.
*H05G 1/00*   (2006.01)
*A61B 6/04*   (2006.01)

(52) U.S. Cl. ........................................ 378/208; 378/37

(58) Field of Classification Search ............ 378/37, 378/208; 264/328.1; 523/128
See application file for complete search history.

(56) References Cited

U.S. PATENT DOCUMENTS

| 4,691,333 | A | * | 9/1987 | Gabriele et al. | 378/37 |
| 5,311,883 | A | * | 5/1994 | Sherman | 128/846 |
| 5,393,804 | A | * | 2/1995 | George et al. | 523/128 |
| 2006/0262899 | A1 | | 11/2006 | Al-Khalidy et al. | |
| 2007/0262489 | A1 | | 11/2007 | Fischbach et al. | |
| 2008/0142721 | A1 | | 6/2008 | Spahn | |

FOREIGN PATENT DOCUMENTS

DE    102004052614    5/2006

* cited by examiner

*Primary Examiner*—Irakli Kiknadze
(74) *Attorney, Agent, or Firm*—Schiff Hardin LLP

(57) ABSTRACT

In a method for production of a compression tray 1 for mammography apparatuses, a thermoplastic synthetic granulate is heated and introduced into an injection mold under pressure in an injection molding procedure.

12 Claims, 4 Drawing Sheets

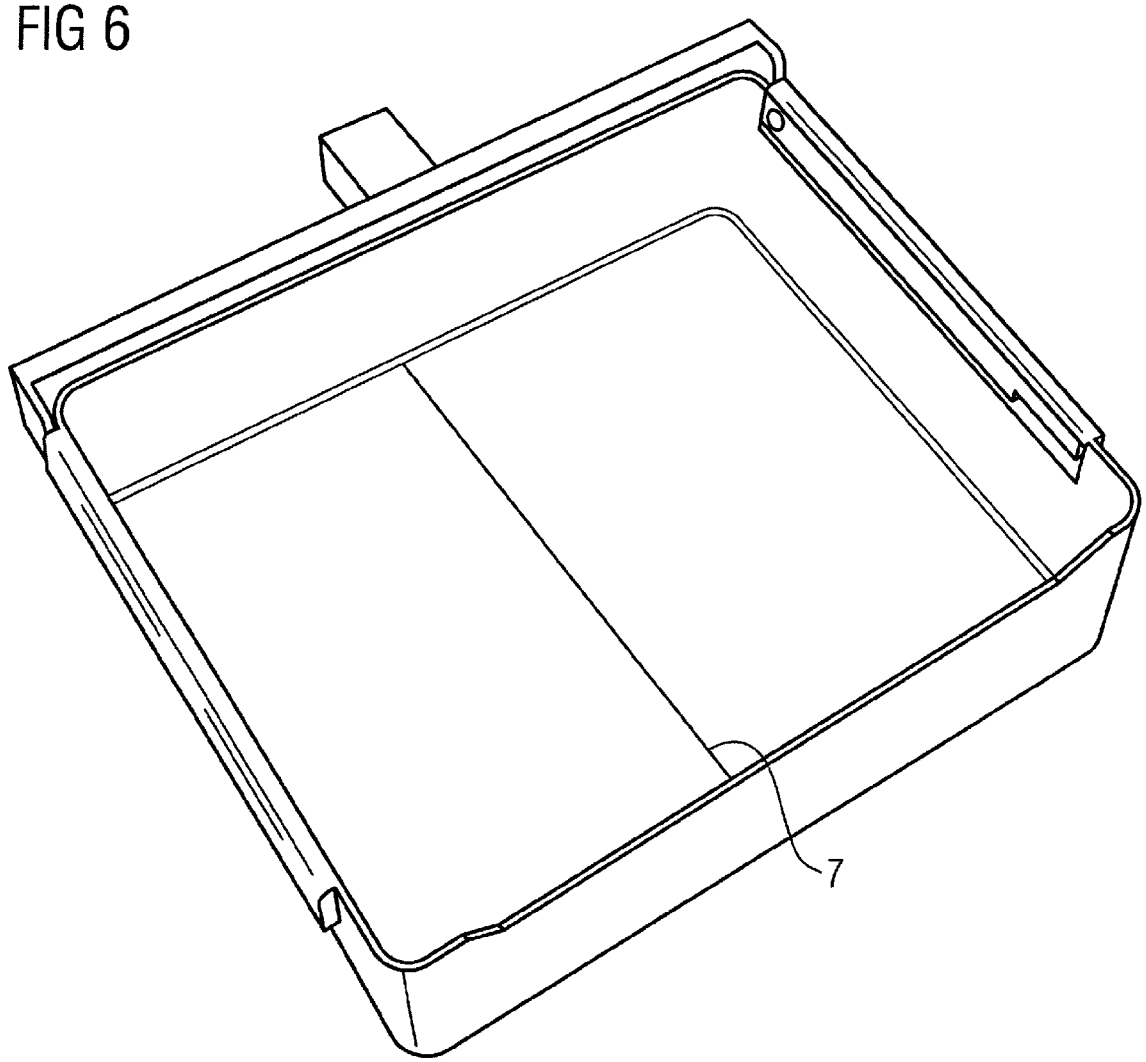

MAMMOGRAPHY APPARATUS COMPRESSION TRAY, AND MOUNTING AND MANUFACTURING METHOD THEREFOR

BACKGROUND OF THE INVENTION

1. Field of the Invention

The present invention relates to a compression tray of the type used in a mammography apparatus, as well as to a method for the manufacture of such a compression tray and a mounting for such a compression tray.

2. Description of the Prior Art

In mammography, compression plates are used in order to place and to compress the female breast on the subject table for the x-ray acquisition. The breast should optimally be compressed with a uniform thickness. The material of the compression tray must be x-ray-resistant since the compression tray is located directly in the beam path. A uniform material thickness must be present in the irradiation region in order to avoid contrast fluctuations. It should be possible to remove the compression tray from the retainer without tools in order to clean and disinfect the compression tray.

Known compression trays made of PC (Lexan) are produced in a deep-draw method. For this the PC plate must be dried for a longer time in an oven in order to be able to be subsequently heated to the deformation temperature. The material can then be brought into a positive or negative deep-draw shape by the application of a vacuum. The wall thickness of the initial material is thereby reduced by up to 50%.

Very different wall thicknesses that become apparent in a contrast attenuation in the x-ray exposure are created by the deep-draw method. After the deep-draw process, the excess material must be mechanically removed. Extreme stresses are introduced in the material by the deep-draw process. PC is not resistant to alcohol-containing cleaning agents. Given their use, ultra-fine surface cracks are generated that can lead to a breakage of the compression tray. The known compression trays are mechanically rigidly connected with the mount and can only be removed with a tool. These require a mechanical connection part in order to transfer the compression force from the tray to the mount.

SUMMARY OF THE INVENTION

An object of the present invention is to avoid the disadvantages connected with the known compression trays.

in accordance with the present invention, a compression tray for a mammography apparatus is produced from a thermoplastic synthesis wherein granulate thermoplastic material is heated and introduced into an injection mold under pressure in an injection molding procedure wherein the compression tray is produced by injection molding.

Also in accordance with the present invention, an injection-molded compression tray is provided with a flexible locking mechanism and a compression tray holder of the mammography apparatus has an element that engages the locking mechanism of the compression tray.

DESCRIPTION OF THE DRAWINGS

FIG. 6 shows in a schematic manner a detail view of a compression tray according to the invention according to a preferred embodiment of the invention, with a center line as a positioning aid.

DESCRIPTION OF THE PREFERRED EMBODIMENTS

Figure 1:
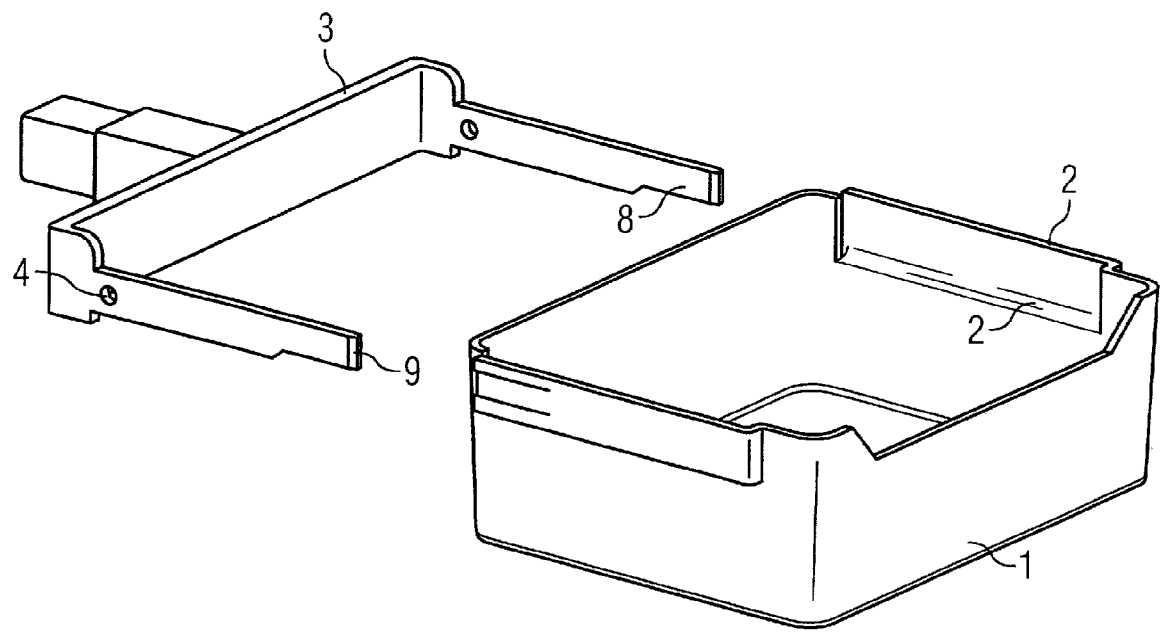
FIG. 1 shows in a schematic manner a compression tray according to the invention with the corresponding mounting, according to a preferred embodiment of the invention.
Figure 2:
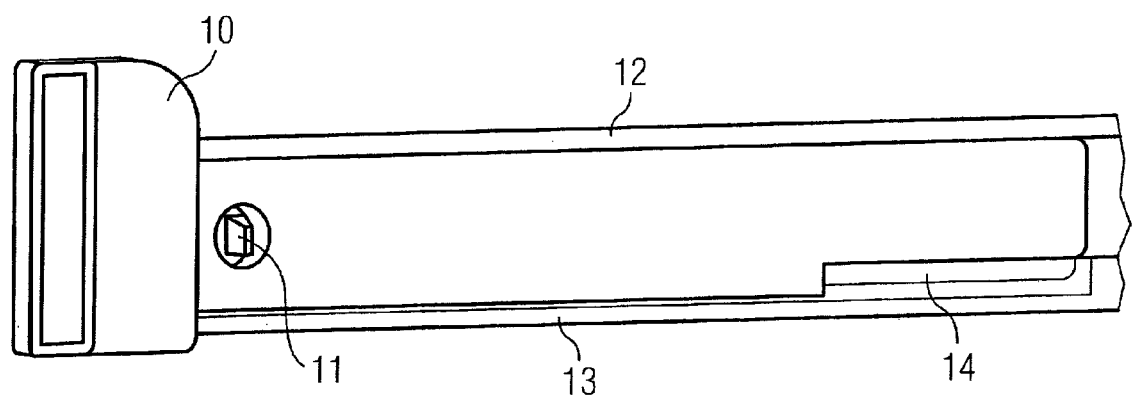
FIG. 2 shows in a schematic manner a detail view of a compression tray according to the invention, attached to a corresponding mounting, according to a preferred embodiment of the invention.
Figure 3:
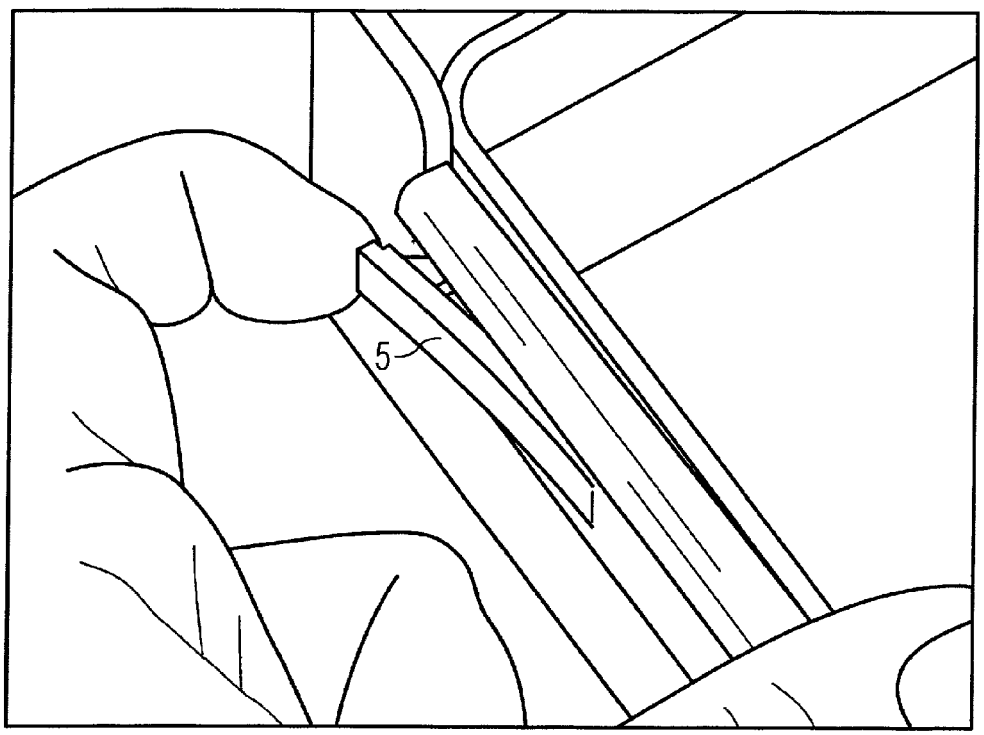
FIG. 3 shows in a schematic manner a detail view of a compression tray according to a preferred embodiment of the invention, in which the lifting of the snapper is shown in detail.
Figure 4:
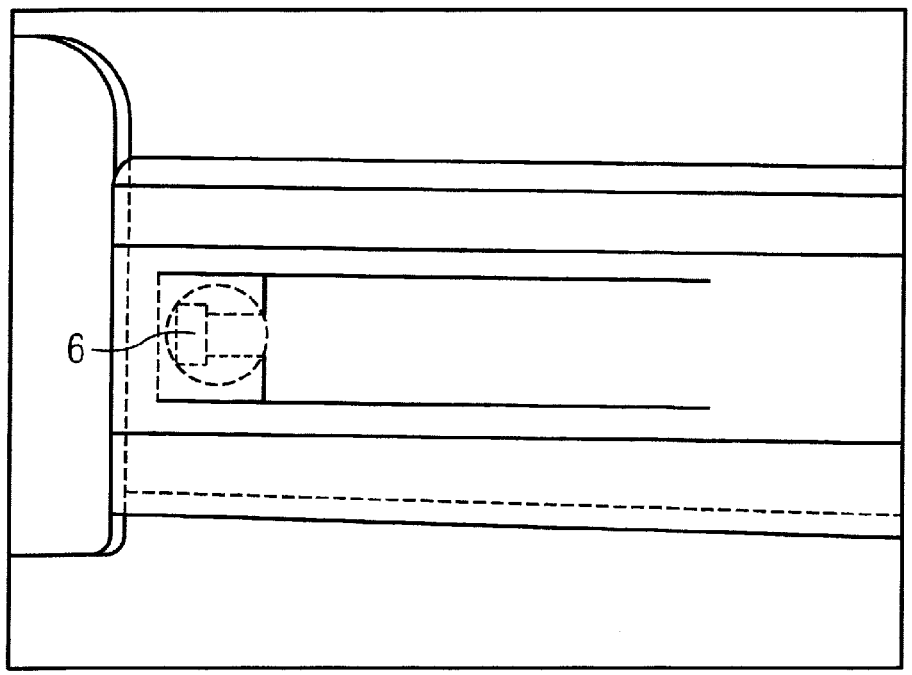
FIG. 4 shows in a schematic manner a detail view of a compression tray according to the invention, attached to a corresponding mounting, according to a preferred embodiment of the invention, in which the snapper is shown in the latched state.
Figure 5:
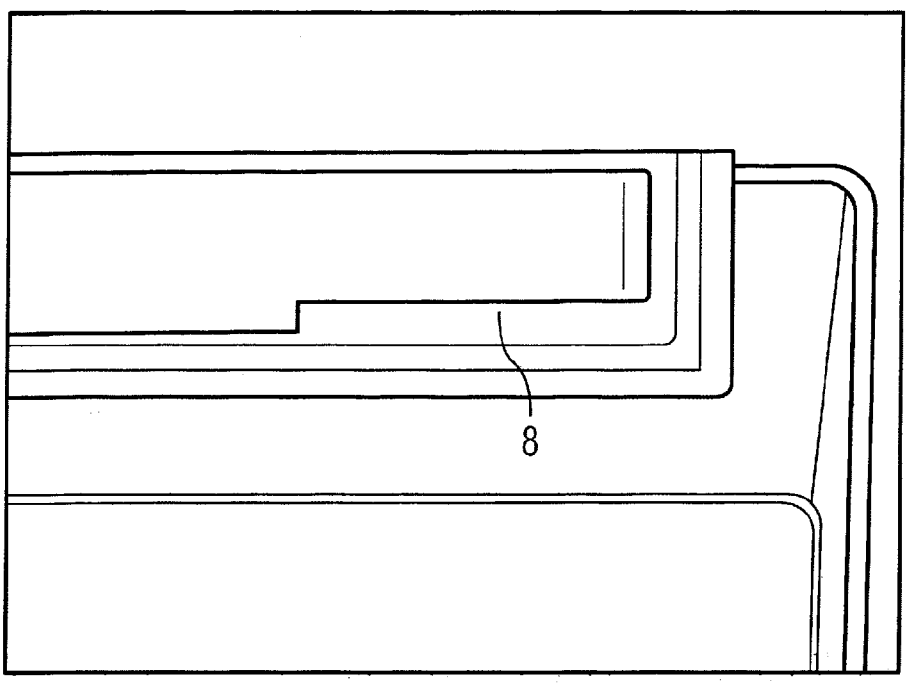
FIG. 5 shows in a schematic manner a detail view of a compression tray according to the invention, attached to a corresponding mounting, according to a preferred embodiment of the invention, in which the mechanical coding is shown in detail.

The compression tray 1 according to the invention is produced in an injection molding method, advantageously from polyethylene terephthalate (PET). A granulate is hereby heated (advantageously via a screw) and is introduced into an injection mold under high pressure. In this production method, practically no stresses are introduced into the compression tray, and the material thickness across the entire compression tray is always uniform. This is due to a correspondingly high dimensional accuracy that is very desirable. PET is resistant to all known alcohol-containing cleaning and disinfection agents.

Polyethylene terephthalate (PET) is a thermoplastic synthetic from the polyester family, produced via polycondensation. PET is polar; strong inter-molecular forces are thereby present. The molecule is additionally linear in design without cross-linking. Both are requirements for semi-crystalline areas and fibers. A high breaking strength and dimensional stability also result due to these areas.

Other plastics with similar properties are likewise suitable for realization of the present invention.

Since the compression tray is created in an injection mold, markings of any type and shape-imparting contours can be applied to the compression tray in this injection molding method.

According to one advantageous development of the invention, the compression tray is produced with parallel lateral guide beads 2 that enable an insertion of the finished compression tray into a mounting or holder 3 at the mammography apparatus.

According to a further embodiment of the invention, the compression tray is produced with at least one locking mechanism 4 that enables locking of the finished compression tray 1 upon insertion into a mounting 3 at the mammography apparatus.

According to a further embodiment of the invention, the locking mechanism is formed by a flexible, resilient tongue known as a snapper that can engage in a corresponding element 6 of the mounting upon insertion.

In another embodiment of the invention, the compression tray is equipped with a line-like marking 7 for adjustment or positioning of the examination subject.

The compression tray according to the invention can particularly advantageously be used with a mounting for a compression tray that is equipped with an element 6 in which the locking mechanism of the compression tray can engage.

In another embodiment of the invention, this mounting is equipped with a mechanical coding 8 to avoid mix-ups of the compression tray.

According to a further embodiment of the invention, this mounting is equipped with a phase for threading 9 the guide beads 2 in the mounting 3.

The two guides 2 pass the force of approximately 200 Newtons that occurs during the compression to the mount. This is achieved by the mount adjoining the compression tray along its entire surface. No additional transfer elements are required this way.

In the exemplary embodiments, the compression tray according to the invention can also be removed from the mount without tools. Respective snappers are lifted on the left and right with the fingertip or fingernail. The compression tray can now be removed from the mount from the front. Upon reattaching the compression tray, this must merely be slid on to the mount until the snappers latch and the compression tray is firmly locked. Given threading, the snappers are automatically raised via a phase. A mechanical coding in the mount is additionally present that prevents a wrong compression tray from being slid onto the mount. The compression tray is advantageously provided with a center line in order to facilitate the positioning of the subject.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for manufacturing a compression tray for a mammography apparatus, comprising the steps of:
   heating a thermoplastic synthetic granulate;
   introducing the heated thermoplastic synthetic granulate into an injection mold configured with a mold shape for a mammography apparatus compression tray; and
   operating said injection mold under pressure in an injection molding procedure to produce a mammography apparatus compression tray from the heated thermoplastic synthetic granulate.

2. A method as claimed in claim 1 comprising employing a thermoplastic synthetic granulate consisting of polyethylene terephthalate.

3. A method as claimed in claim 1 comprising heating said thermoplastic synthetic granulate with a heated screw.

4. A method as claimed in claim 1 comprising, in said injection mold, providing a mold portion configured to form parallel lateral guide beads on said compression tray that enable insertion of the compression tray into a mounting of a mammography apparatus.

5. A method as claimed in claim 1 comprising, in said injection mold, providing a mold portion configured to form at least one locking mechanism on said compression tray that enables locking of the finished compression tray upon insertion into a mounting of a mammography apparatus.

6. A method as claimed in claim 5 comprising forming said injection mold portion to produce said locking mechanism as a flexible tongue configured to engage a complementary element of said mounting upon insertion of the finished compression tray into said mounting.

7. A method as claimed in claim 1 comprising in said injection molding procedure, providing said compression tray with a line-like marking allowing adjustment or positioning of an examination subject relative to the finished compression tray.

8. A compression tray for a mammography apparatus, comprising:
   an injection-molded tray configuration formed of a thermoplastic synthetic granulate consisting of polyethylene terephthalate that is heated and introduced into an injection mold under pressure in an injection molding procedure.

9. A compression tray as claimed in claim 8 comprising parallel lateral guide beads on opposite sides thereof configured to allow insertion of the compression tray into a mounting of said mammography apparatus.

10. A compression tray as claimed in claim 9 comprising at least one locking mechanism configured to lock the compression tray into said mounting.

11. A compression tray as claimed in claim 10 wherein said locking mechanism comprises a flexible tongue configured to engage a complementary element of said mounting upon insertion of said compression tray into said mounting.

12. A compression tray as claimed in claim 8 comprising a line-like marking thereon allowing adjustment or positioning of an examination subject relative to the compression tray.

* * * * *